US012616830B2

(12) United States Patent
Park et al.

(10) Patent No.: US 12,616,830 B2
(45) Date of Patent: May 5, 2026

(54) LEAD STRUCTURE FOR APPLYING ELECTRICAL STIMULATION TO BODY ORGAN, AND ELECTRODE SYSTEM USING SAME

(71) Applicant: SAMSUNG LIFE PUBLIC WELFARE FOUNDATION, Seoul (KR)

(72) Inventors: Eun Kyoung Park, Seoul (KR); Tae Kyung Kim, Seoul (KR); Tae Woo Kim, Seoul (KR); Dong Il Choi, Seoul (KR); Kyu Sung Lee, Seoul (KR)

(73) Assignee: SAMSUNG LIFE PUBLIC WELFARE FOUNDATION (KR)

( * ) Notice: Subject to any disclaimer, the term of this patent is extended or adjusted under 35 U.S.C. 154(b) by 672 days.

(21) Appl. No.: 17/921,958

(22) PCT Filed: Mar. 30, 2021

(86) PCT No.: PCT/KR2021/003942
§ 371 (c)(1),
(2) Date: Oct. 27, 2022

(87) PCT Pub. No.: WO2021/221322
PCT Pub. Date: Nov. 4, 2021

(65) Prior Publication Data
US 2023/0173258 A1 Jun. 8, 2023

(30) Foreign Application Priority Data
Apr. 28, 2020 (KR) ........................ 10-2020-0051333

(51) Int. Cl.
*A61N 1/05* (2006.01)
*A61N 1/36* (2006.01)
*A61N 1/375* (2006.01)

(52) U.S. Cl.
CPC ....... *A61N 1/0534* (2013.01); *A61N 1/36125* (2013.01); *A61N 1/36128* (2013.01); *A61N 1/37514* (2017.08); *A61N 1/3752* (2013.01)

(58) Field of Classification Search
CPC .............. A61N 1/0534; A61N 1/37514; A61N 1/3606; A61N 1/0539; A61N 1/375;
(Continued)

(56) References Cited

U.S. PATENT DOCUMENTS 5,190,052 A * 3/1993 Schroeppel ............ A61N 1/056
600/375
2001/0008972 A1* 7/2001 Gielen ............... A61N 1/36153
607/45
(Continued)

FOREIGN PATENT DOCUMENTS

KR 10-1033749 B1 5/2011
KR 10-2020-0016103 A 2/2020

OTHER PUBLICATIONS

International Search Report of WIPO in Application No. PCT/KR2021/003942, filed Mar. 30, 2021.

*Primary Examiner* — Carl H Layno
*Assistant Examiner* — Anh-Khoa N Dinh
(74) *Attorney, Agent, or Firm* — Dilworth IP, LLC

(57) ABSTRACT
A lead structure includes a lead having an electrode wire having one end provided as an insertion portion to be inserted into a body and the other end provided as an interface portion for connection with an external device, a first electrode in the insertion portion to transmit electrical stimulation to body organs, a second electrode on the interface portion to receive electrical stimulation applied from outside, and a signal line configured to interconnect the first electrode and the second electrode and transmit the electrical stimulation received by the second electrode to the first electrode; and a lead case configured to surround the
(Continued)

lead, and a conductive plate configured to apply electrical stimulation to body organs and a support plate configured to provide electrical stimulation from the first electrode to the conductive plate by contacting the first electrode.

5 Claims, 7 Drawing Sheets

(58) Field of Classification Search
  CPC ............ A61N 1/36067; A61N 1/36096; A61N 1/36125; A61N 1/36128; A61N 1/0456; A61N 1/0472; A61N 1/0476; A61N 1/0526; A61N 1/3603; A61N 1/36036; A61N 1/00; A61N 1/04; A61N 1/05; A61N 1/18; A61N 1/32; A61N 1/36021; A61N 1/36034; A61N 1/372; A61N 1/3752
  See application file for complete search history.

(56) References Cited

U.S. PATENT DOCUMENTS

| | | | |
|---|---|---|---|
| 2004/0176831 A1* | 9/2004 | Gliner .................. | A61N 1/0531 607/142 |
| 2005/0222657 A1* | 10/2005 | Wahlstrand .......... | A61N 1/0534 607/116 |
| 2010/0268298 A1 | 10/2010 | Moffitt et al. | |
| 2010/0331938 A1 | 12/2010 | Sommer et al. | |
| 2012/0158077 A1* | 6/2012 | Buessing ............... | A61N 1/056 607/8 |
| 2016/0144189 A1* | 5/2016 | Bakker ................ | A61B 5/6868 607/45 |
| 2017/0291024 A1 | 10/2017 | Kurtev | |
| 2020/0037957 A1 | 2/2020 | Hjelle et al. | |

* cited by examiner

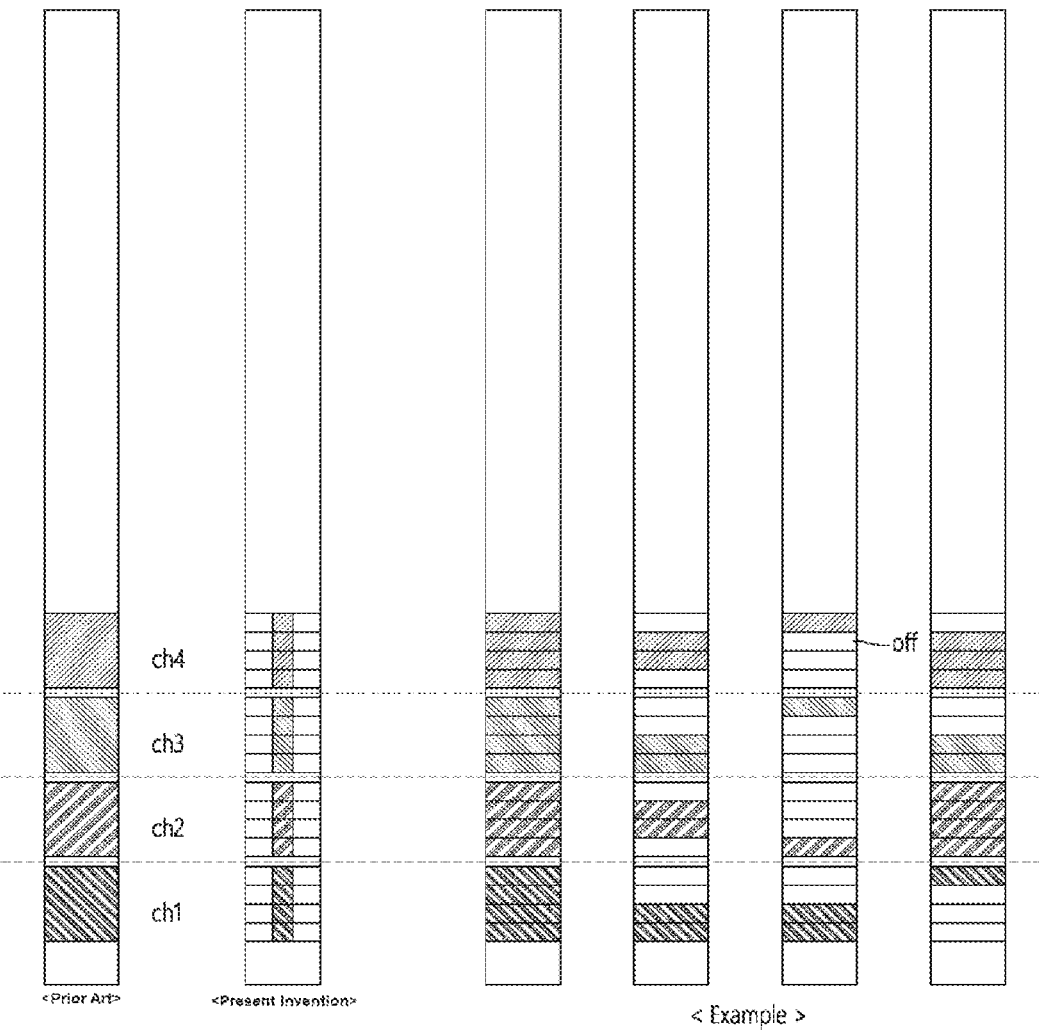
FIG. 5A                    FIG. 5B

LEAD STRUCTURE FOR APPLYING ELECTRICAL STIMULATION TO BODY ORGAN, AND ELECTRODE SYSTEM USING SAME

FIELD OF THE INVENTION

The present invention relates to a lead structure for applying electrical stimulation to body organs and a lead system using the same.

BACKGROUND OF THE INVENTION

Due to the complexity of modern society, modern people are easily exposed to accidents or diseases and lose their intrinsic functions or exercise abilities, but there is a limit to healing these patients with medicine alone. In order to overcome these limitations, the field of biomedical engineering, which was created by grafting the technology of the engineering field with the medical field, is developing, and as a result, major changes are occurring in many areas of a health care system.

For example, pacemakers and ventricular defibrillators are saving many lives and playing an innovative role in the treatment of heart disease. In addition, using pacemaker technology, the surgeon implants a Deep Brain Stimulation (DBS) device into the patient's brain to control an abnormal brain function (e.g., see patent documents).

Abnormal physical behavior or mental disorders result from abnormal functions of the brain, such as Parkinson's Disease (PD) or Obsessive-Compulsive Disorder (OCD). PD is a chronic degenerative brain disease in which the main symptoms are trembling hands and feet, slow movements, and stiff muscles, and OCD is a mental disorder in which people are reluctant to go out because of fear that they may be contaminated by things they come in contact with.

Neurosurgeons are now using deep brain stimulators to treat serious health problems such as Parkinson's disease, obsessive-compulsive disorder and depression. A treatment method using a deep brain stimulator is a surgical method, and it is the only hope for treating obsessive-compulsive disorder and is evaluated as a method that has been proven effective in curing Parkinson's disease.

Deep brain stimulation utilizes implantable medical devices to deliver accurate electric pulses. A deep brain stimulator is largely composed of an implantable pulse generator, an extension, and a lead.

In general, when an implantable pulse generator is implanted under the chest subcutaneously, a lead is placed deep in a specific region of the brain, and the two components are connected to each other with an extension to generate stimulation through the implantable pulse generator, the stimulation is transmitted to the lead through the extension, and microelectrical stimulation may be applied to the specific region of the brain through the lead.

It is important to check the position and contact point of the lead after surgery because the clinical course may differ for each patient depending on the position of the lead. Accordingly, during deep brain stimulation and lead implantation surgery, it is necessary to check an electrode stimulation position through various measurement methods such as MRI, CT image, C-arm image, and cranial nerve signal. However, if sufficient micro-electrical stimulation is not made to a correct target, it is difficult to expect a therapeutic effect.

However, in the case of a conventional lead, although sizes and positions of electrode contact points are constant, each person has a different target position and size, so it is difficult to accurately match the lead to the target, but this problem is not considered in the prior art.

SUMMARY OF THE INVENTION

The present invention provides a lead and a lead system capable of adjusting a contact point and a position of an electrode from the outside.

The present invention also provides a lead structure capable of adjusting a size or position of an electrode contact point after inserting a lead into the body, and a lead system using the same.

As an embodiment of the present disclosure, a lead structure configured to apply electrical stimulation to body organs may be provided.

The lead structure according to an embodiment of the present disclosure may include: a lead comprising an electrode wire having one end provided as an insertion portion to be inserted into a body and the other end provided as an interface portion for connection with an external device, a first electrode in the insertion portion to transmit electrical stimulation to body organs, a second electrode on the interface portion to receive electrical stimulation applied from outside, and a signal line configured to interconnect the first electrode and the second electrode and transmit the electrical stimulation received by the second electrode to the first electrode; and a lead case configured to surround the lead, wherein a key hole penetrating from an inside to an outer surface is formed in a longitudinal direction at a position of the first electrode in the electrode wire, a slot extending in the longitudinal direction is formed at the position of the first electrode in the lead case, and a conductive plate configured to apply electrical stimulation to body organs and a support plate configured to provide electrical stimulation from the first electrode to the conductive plate by contacting the first electrode are provided, wherein the conductive plate and the support plate are provided on an outer surface and an inner surface of the lead case, respectively, and are coupled to each other with a slot therebetween to form a pair, and a plurality of pairs of a conductive plate and a support plate are provided and arranged to be movable along the slot.

The lead structure according to an embodiment of the present disclosure may further include the conductive plate and the support plate are coupled by an elastic connecting member passing through the slot and movably arranged in the lead case.

The lead structure according to an embodiment of the present disclosure may further include the support plate is formed with a through hole into which a tip of a plate key for moving the support plate is inserted.

As an embodiment of the present disclosure, a lead structure configured to apply electrical stimulation to body organs may be provided.

The lead structure according to an embodiment of the present disclosure may include: an electrode wire having one end provided as an insertion portion to be inserted into a body and the other end provided as an interface portion for connection with an external device, a first electrode in the insertion portion to transmit electrical stimulation to body organs, a second electrode on the interface portion to receive electrical stimulation applied from outside, and a signal line configured to interconnect the first electrode and the second electrode and transmit the electrical stimulation received by the second electrode to the first electrode; and a lead case configured to surround the lead, wherein, in the electrode wire, a plurality of slots extending in a circumferential direction on an opposite side of the circumferential direction with respect to the first electrode are formed to be apart from each other in a longitudinal direction, a plurality of ring-shaped conductive plates are provided at a position of the lead case corresponding to the first electrode, and each of the conductive plates is rotated in a circumferential direction by a key inserted through the slot and is selectively electrically connected to the first electrode.

The lead structure according to an embodiment of the present disclosure may further include a contact point capable of contacting the first electrode is formed at a certain position in the circumferential direction on an inner surface of the conductive plate of the lead case, and the conductive plate rotates so that the contact point come into contact with the first electrode, thereby electrically connecting the conductive plate and the first electrode.

The lead structure according to an embodiment of the present disclosure may further include a groove is formed on an inner surface of the conductive plate of the lead case, a tip of a plate key for rotating the conductive plate is inserted into the groove, and the plate key rotates to rotate the conductive plate.

As an embodiment of the present disclosure, a lead structure configured to apply electrical stimulation to body organs may be provided.

The lead structure according to an embodiment of the present disclosure may include: an electrode wire having one end provided as an insertion portion to be inserted into a body and the other end provided as an interface portion for connection with an external device, a first electrode in the insertion portion to transmit electrical stimulation to body organs, a second electrode on the interface portion to receive electrical stimulation applied from outside, and a signal line configured to interconnect the first electrode and the second electrode and transmit the electrical stimulation received by the second electrode to the first electrode; and a lead case configured to surround the lead, wherein the first electrode extends in a longitudinal direction of the electrode wire, a plurality of first electrodes are arranged to be apart from each other in a circumferential direction, a plurality of slots extending in the circumferential direction and apart from each other in the longitudinal direction are formed in the electrode wire on an opposite side of the circumferential direction with respect to the first electrodes, a plurality of ring-shaped conductive plates are provided at a position of the lead case corresponding to the second electrode, and each conductive plate is rotated in the circumferential direction by a key inserted through a slot to be selectively electrically connected to any one of the first electrodes.

The lead structure according to an embodiment of the present disclosure may further include a contact point capable of contacting the first electrode is formed at a certain position in the circumferential direction on an inner surface of the conductive plate of the lead case, and the conductive plate rotates so that the contact point come into contact with any one of the first electrodes, thereby electrically connecting the conductive plate and the first electrode.

The lead structure according to an embodiment of the present disclosure may further include a groove is formed on an inner surface of the conductive plate of the lead case, a tip of a plate key for rotating the conductive plate is inserted into the groove, and the plate key rotates to rotate the conductive plate.

As an embodiment of the present disclosure, a lead system implanted in a body to apply electrical stimulation to body organs may be provided.

The lead system according to an embodiment of the present disclosure may include: a main processor connected to an external device for communication and control; one or more lead structures; an electrode clamp for electrical connection with the lead; and a controller for controlling a position of transmitting electrical stimulation in the lead.

The lead system according to an embodiment of the present disclosure may further include the controller comprises a key capable of movement in a longitudinal direction of an electrode wire and rotational movement in a circumferential direction, and the key is inserted into a hollow of the electrode wire to move or rotate a conductive plate along a slot.

According to the present invention, by changing a position of an electrode contact point through external control, the position or the electrode spacing may be adjusted according to a stimulation target.

BRIEF DESCRIPTION OF DRAWINGS

FIGS. 5A and 5B show a signal aspect obtained by the lead structure according to the second embodiment (FIG. 5B) with the prior art (FIG. 5A).

DETAILED DESCRIPTION OF THE INVENTION

Figure 1:
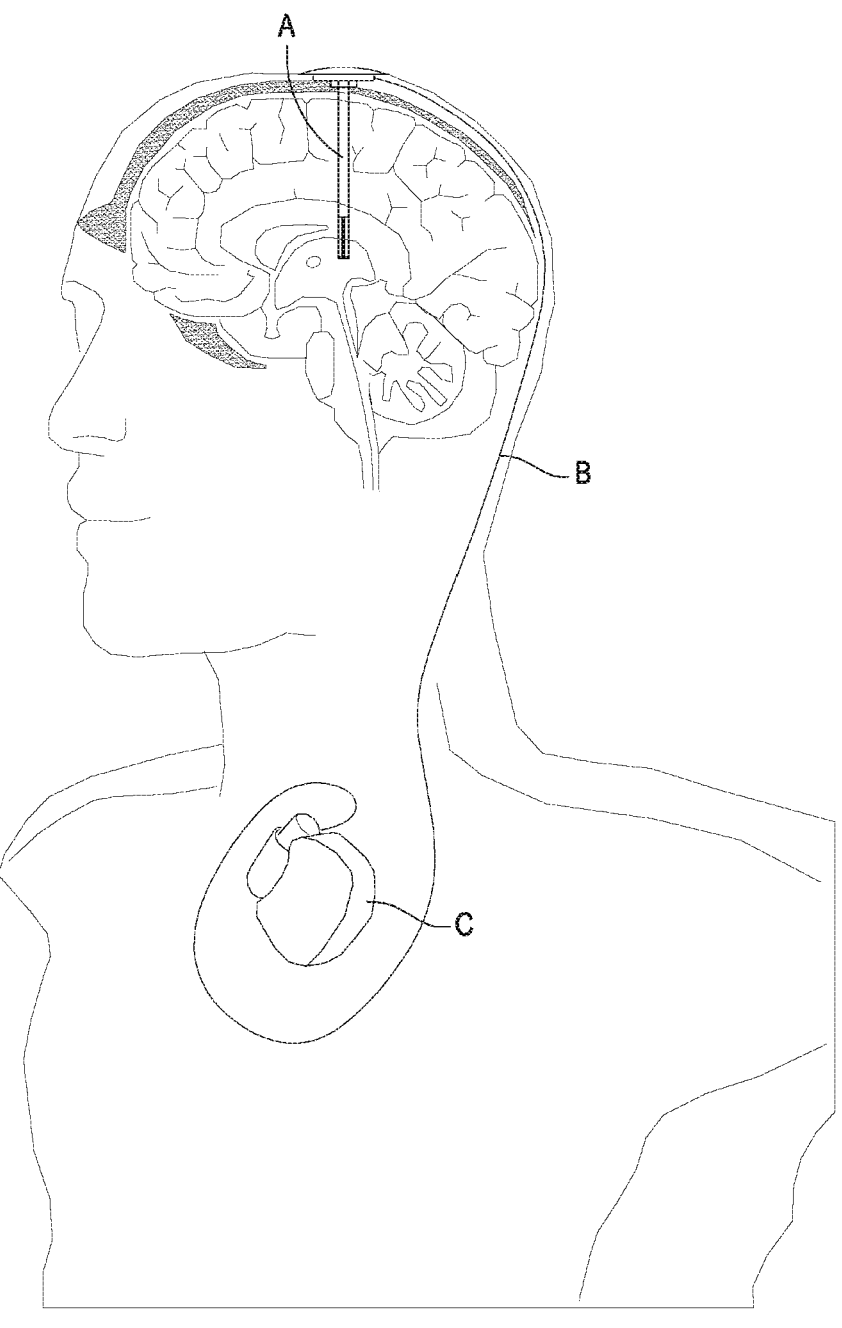
FIG. 1 schematically shows a state in which a deep brain stimulator targeted by the present invention is applied to the body.

Hereinafter, embodiments in which a lead structure and a lead system according to the present invention are applied to a deep brain stimulator will be described with reference to the drawings.

In the following description, descriptions of the already known technical configuration and operation in relation to the deep brain stimulator will be omitted. For example, descriptions of a configuration/structure/method of a device or system commonly used in deep brain stimulation, such as the structure of an implantable pulse generator, a connection structure/method of the implantable pulse generator and a lead, and a process for transmitting and receiving electrical signals measured through the lead with an external device, will be omitted. Even if these descriptions are omitted, one of ordinary skill in the art will be able to easily understand the characteristic configuration and operation of the present invention through the following description.

Each component shown in the drawings is merely illustrative or schematic, and the present invention is not limited to the illustrated configuration. In addition, the material of each component will not be described in detail. That is, the present invention is not particularly limited to the material of each component.

FIG. 1 schematically shows a state in which a deep brain stimulator targeted by the present invention is applied to the body. As shown, the deep brain stimulator includes a plurality of leads A (only one is shown in FIG. 1) implanted in a specific region of the brain, an implantable pulse generator C implanted subcutaneously in the chest, and an extension connecting the leads to the implantable pulse generator.

When electrical stimulation is generated through the implantable pulse generator, the electrical stimulation is transmitted to a lead through the extension, and micro-electrical stimulation may be applied to a specific region of the brain through the lead.

An embodiment described below relates to a lead system for a deep brain stimulator that enables implantation of a lead A from among components of the deep brain stimulator into a target in a specific region of the brain accurately and with a simple procedure, and a lead structure.

Accordingly, as described above, descriptions of an implantable pulse generator, an extension, a connection structure/method of a lead and an extension, and an operation of a deep brain stimulator including an implantable pulse generator, which do not constitute the features of the present invention, will be omitted.

Figure 2:
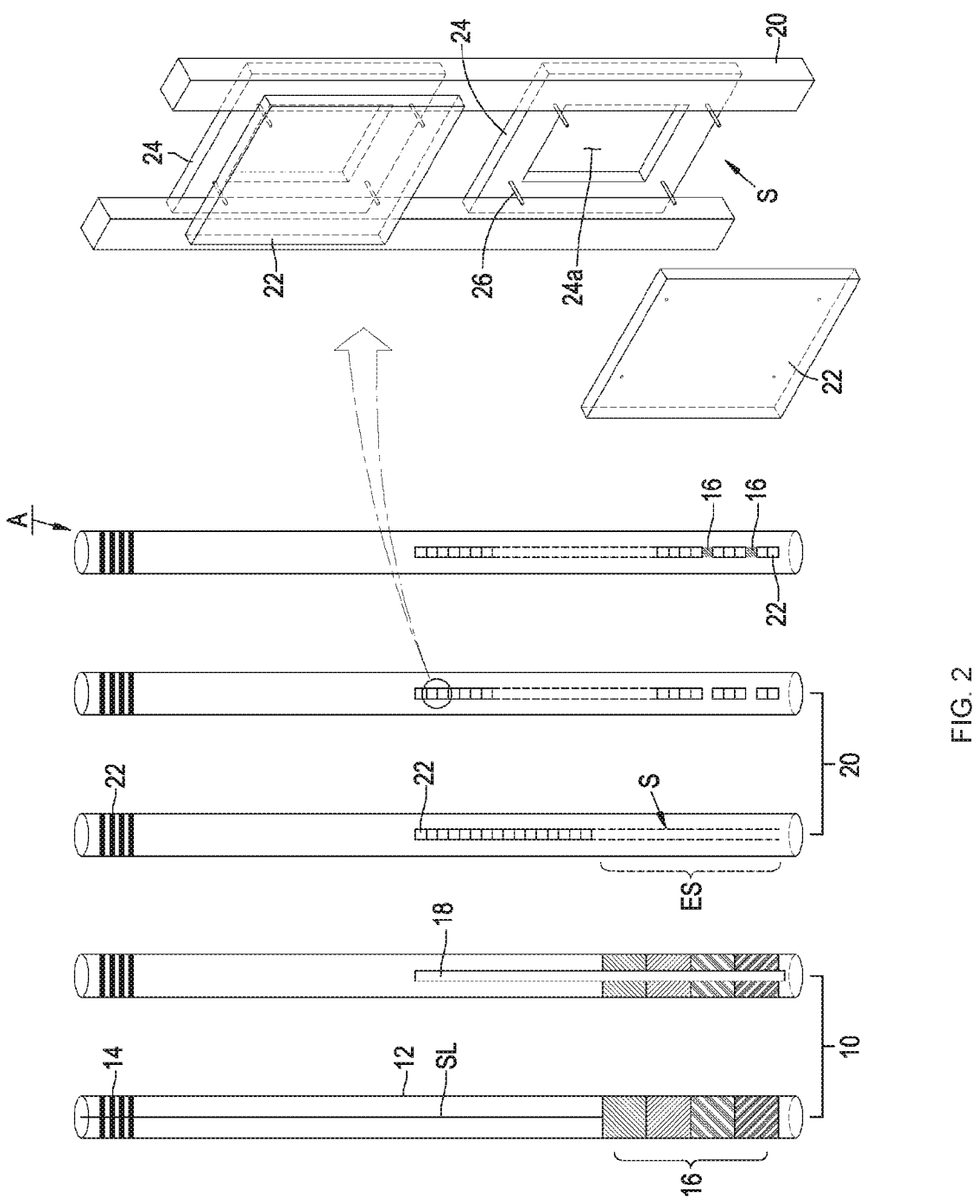
FIG. 2 is an enlarged view of a configuration and a portion of a lead structure for a deep brain stimulator according to a first embodiment of the present invention.

FIG. 2 is an enlarged view of a configuration and a portion of a lead structure for a deep brain stimulator according to a first embodiment of the present invention.

As shown, the lead structure A includes a lead 10 and a lead case 20 formed to surround the lead 10. The lead 10 includes an electrode wire 12 transmitting a stimulation signal from a brain region into which the electrode wire is inserted, first and second electrodes 16 and 14 provided at both ends of an electrode wire, and a signal line SL interconnecting the electrodes at both ends.

On the other hand, in the drawing, the first electrode 16 provided in a lower portion of the electrode wire, that is, an insertion portion to be inserted into the brain, has a C-shaped cross section, unlike the second electrode 14 provided in an upper portion, that is, an interface portion for connection with the implantable pulse generator C (FIG. 1).

In other words, a portion of the first electrode 16 is cut to form a path through which a plate key 32 (in FIG. 3) to be described later may move in a vertical direction of the electrode wire.

In addition, as shown, a portion of the electrode wire 10 is cut in a longitudinal direction to form a key hole 18 continuous to the path formed by the cutout of the electrode 16.

Accordingly, when the plate key 32 to be described later is inserted into an inner hollow space of the electrode wire 10 and moved in the longitudinal direction of the electrode wire 10, an end of the plate key 32 (in FIG. 3) protrudes through the key hole 18 to move a conductive plate of the lead case 20 to be described later.

In FIG. 2, the signal line SL is in a form fixed to the outside of the electrode wire, but the present invention is not particularly limited to the form of the signal line. That is, as long as the signal line is connected to electrodes provided at upper and lower ends of the electrode wire, the signal line is not limited to a form fixed to a surface of the electrode wire 10, and may be fixed, for example, by being inserted into the electrode wire 10 or an inner wall of the electrode wire 10.

The electrode wire 10 is flexible and has excellent durability, and is formed of a material harmless to the human body, for example, polyurethane. On the other hand, although not specifically illustrated, the electrode wire 10 includes a guide wire that is inserted into an inner space of the electrode wire and supports the electrode wire when the electrode wire is inserted.

The lead case 20 is a member provided in a shape surrounding the lead 10, wherein an electrode 22 is formed on an upper end of the lead case 20 and at positions of inner and outer walls corresponding to the second electrode 14 of the lead 10, and is connected to the second electrode 14 of the lead so that a signal may be transmitted.

Accordingly, an electrical signal input to the electrode 22 of the lead case may be input to the second electrode 14 of the electrode wire.

In a portion of the lead case 20, a slot S penetrating the wall is formed over a portion of a longitudinal direction of the lead case 20, for example, half of the longitudinal direction. In addition, with the slot S therebetween, a conductive plate 22 is disposed on the outer wall and a support plate 24 is disposed on the inner wall, and they are connected to each other by an elastic connecting member 26.

Accordingly, the conductive plate and the support plate are kept in close contact with a wall surface of the lead case 20 unless an external force is applied. A through hole 24a is formed in a portion of the support plate 24, for example, the center of the support plate 24, and an end of the plate key 32, which will be described later, passes through the through hole 24a to contact the conductive plate 22.

On the other hand, as shown, the conductive plate and the support plate form one set, and a plurality of sets are provided in the lead case 20. A portion of the slot S of the lead case is composed of an empty space ES in which the conductive plate and the support plate are not arranged, and thus, the conductive plate is configured to move into the empty space by a plate key to be described later.

On the other hand, respective positions (e.g., 1 to n) where conductive plates from the bottom to the top with respect to the slot S may be located is coordinated, so that each conductive plate may be located at a required position by external control.

Figure 3:
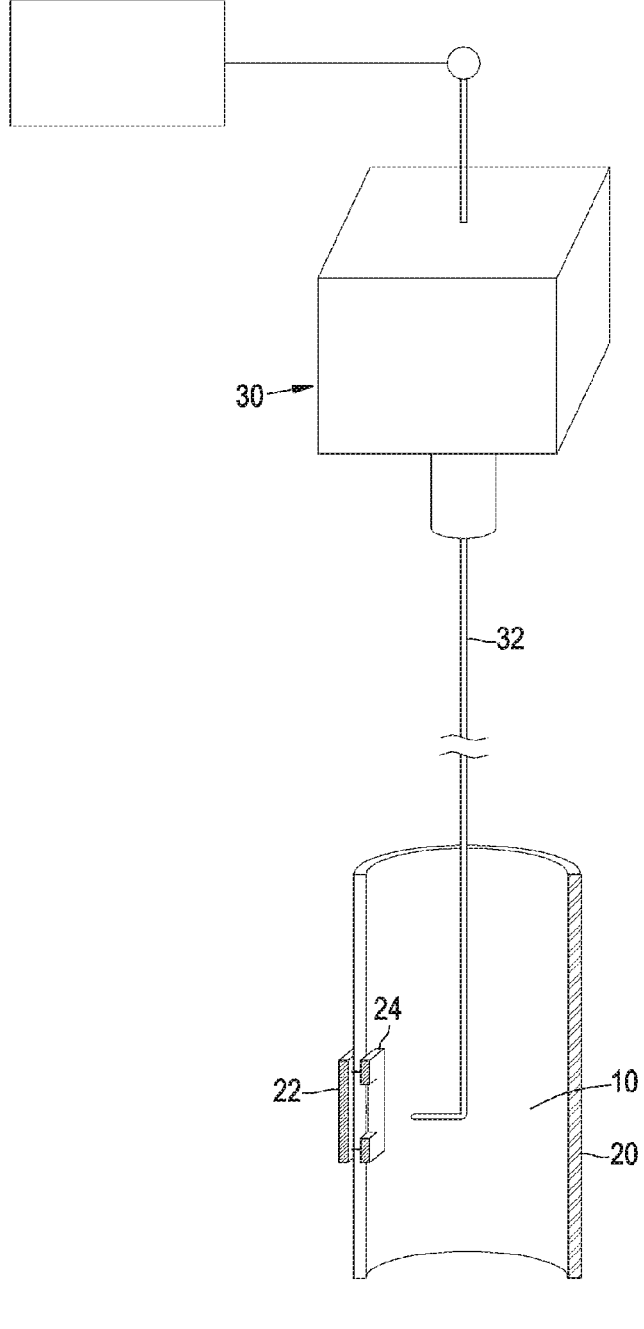
FIG. 3 shows a schematic structure of a plate controller 30 used in one embodiment of a lead implantation system of the present invention.

FIG. 3 shows a schematic structure of a plate controller 30 used in one embodiment of a lead implantation system of the present invention. That is, a lead system of the first embodiment includes a main processor (not shown) in charge of communication and control, an electrode clamp (not shown) for electrical connection with an electrode of a lead, and the plate controller 30 capable of moving the conductive plate 22.

The main processor is connected to a separate external device (PC, tablet, smartphone, etc.) to exchange signals, digitizes an electrical signal measured from an electrode, transmits the electrical signal to the external device, or receives a control signal from the external device to drive a motor.

The electrode clamp has a semicircular structure attached to an end of a clamp with a spring so that electrode clamp may be well attached to a surface of a lead. In the electrode clamp, the lead comes out of a contact point located on one arm of the clamp and is connected to the main processor, and a guide line is attached to the opposite arm to align positions of the lead and the clamp. Because the main processor and the electrode clamp are known components commonly used in the field of deep brain stimulation, a detailed description of the configuration and operation will be omitted herein.

The plate controller 30 includes a linear motor and a rotating motor (not shown) that move by receiving a control signal from the main processor. A plate key is connected to a motor shaft of the linear motor and the rotating motor so that the plate key may move and rotate in a linear direction including a vertical direction corresponding to a longitudinal direction of an electrode wire and a horizontal direction perpendicular to the vertical direction according to driving of the linear motor and the rotating motor. The plate key 32 is movably and rotatably mounted to a support S of the plate controller, and a tip thereof is bent.

When power is applied to the plate controller 30 through a power supply device not shown, motors are driven so that the plate key enters a hollow of the lead 10, and when the motors reach the position of the conductive plate 22 to be moved from among a plurality of conductive plates arranged in the key hole 18, the motors move in a horizontal direction by the linear motor, and a bent end of the plate key passes through the key hole 18 of the lead 10 and is inserted into the through hole 24a mounted on an electrode case 20.

Accordingly, the plate key 32 is coupled to a specific support plate 24, and the plate key 32 moves downward by the motor drive. Accordingly, the conductive plate 22 also moves to a lower empty space ES together with the support plate 24 (see the case of FIG. 2 and FIG. 3).

By repeating this operation for a plurality of conductive plates, the position and interval of stimulation of a target electrode may be adjusted.

That is, although the first electrode 16 of the electrode wire 10 is not exposed and is surrounded by the lead case 20, an electric signal from the first electrode 16 may be transmitted to the conductive plate 22 where the conductive plate 22 is located to apply electrical stimulation to a brain region where the conductive plate 22 is located.

In this way, by adjusting positions of a plurality of conductive plates 22 provided in the lead case 20, positions and intervals at which stimulation is applied are set.

These series of operations may be automatically performed under the control of a control unit connected to the plate controller 30, or may be performed manually while an operator moves a conductive plate using a plate key and checks an electrical stimulation signal transmitted by the conductive plate 22 through a separate display device (not shown).

According to this composition and action, a limited number of first electrodes 16 may be arranged in a fixed position on the electrode wire 10. However, by arranging a larger number of conductive plates 22 than the number of first electrodes in the lead case 20 and adjusting positions of the conductive plates, the position and area to which electrical stimulation from the first electrode is applied may be more precisely controlled. In particular, this adjustment may be made after the lead is inserted into the deep part of the brain.

Figure 4A:
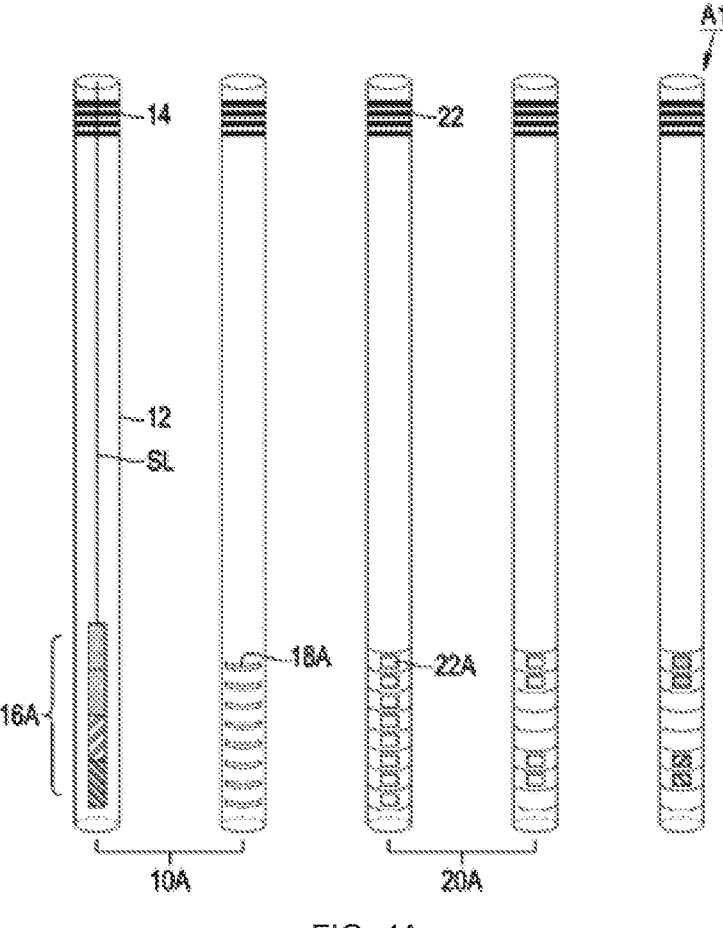
FIG. 4A shows a configuration of a lead structure A1 according to a second embodiment of the present invention.

FIG. 4A shows a configuration of a lead structure A1 according to a second embodiment of the present invention. The lead structure A1 also includes a lead 10A and a lead case 20A, similarly to the lead structure A.

Unlike the lead 10 of the first embodiment, the lead 10A of the second embodiment has a plurality of first electrodes 16A arranged side by side in a longitudinal direction, and the first electrodes 16A are connected to each other by the second electrode 14 of an interface portion and the signal line SL. On the other hand, a plurality of slots 18A extending in a circumferential direction are apart from each other in a longitudinal direction of the lead 10A and are formed in parallel in a position opposite to the position in the circumferential direction with respect to the position where the first electrodes 16A are provided. Each slot is formed over a certain angular range in the circumferential direction.

A plurality of conductive plates 21A having a ring shape are provided under the lead case 20A corresponding to a lead insertion portion. The conductive plates 21A is configured to be rotated in a circumferential direction with respect to the lead case 20A by an external force.

Figure 4B:
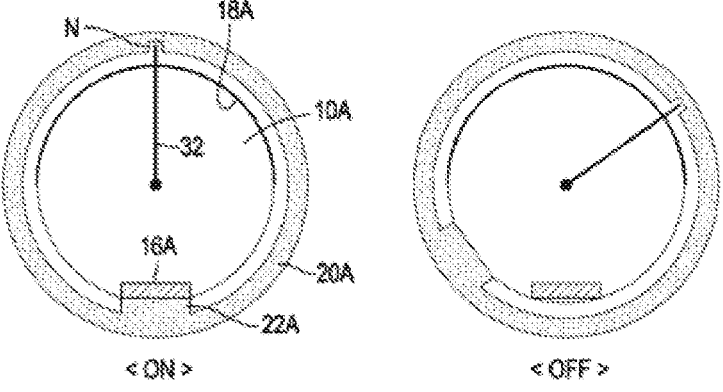
FIG. 4B shows a cross-sectional view of the lead structure A1 of FIG. 4A.

As shown in FIG. 4B, an inner surface of each conductive plate 21A is provided with a connecting portion 22A protruding radially inwardly at a specific position in the circumferential direction, so that when the connecting portion comes into contact with the first electrode 16 of an electrode wire, an electric signal from the first electrode 16 is transmitted to the conductive plate 21A through the connecting portion 22A.

In addition, each conductive plate 21A is provided with a notch portion N into which the plate key 32 may be inserted at a specific position in the circumferential direction, specifically, at a position opposite to the connecting portion 22A with respect to the circumferential direction.

When a tip of the plate key 32 inserted into a hollow of the electrode wire 10A passes through a slot 18A and is inserted into the notch N, the plate key 32 rotates according to motor drive, and thus, when the connecting portion 22A of the conductive plate 21A comes into contact with the first electrode 16A of the electrode wire 10A, the connecting portion 22A is in an ON state in which an electrical signal from the first electrode is transmitted to the conductive plate 21A, so that electrical stimulation may be applied through the conductive plate 21A. When the connecting portion 22A of the conductive plate 21A does not contact the first electrode 16A of the electrode wire 10A, the connecting portion 22A is in an OFF state in which an electrical signal from the first electrode is not transmitted to the conductive plate 21A, and thus, an electrical signal from the first electrode is not transmitted to the conductive plate.

According to the configuration and operation of the lead structure of the second embodiment as described above, a position at which electrical stimulation is applied by the first electrode in a longitudinal direction of the lead structure may be subdivided and adjusted, and target stimulation positions and intervals may be easily set.

That is, as shown in FIG. 5B, by rotating the conductive plate 21A forming a ring shape, whether or not electrical stimulation is transmitted by contact with the first electrode of the lead may be changed and controlled, so that a position of an electrode contact point may be changed according to a stimulation target. Accordingly, compared to the prior art as shown in FIG. 5A, by specifying a contact position in more various aspects, electrical stimulation may be applied to various positions of a brain region into which a lead structure is inserted.

Figure 6A:
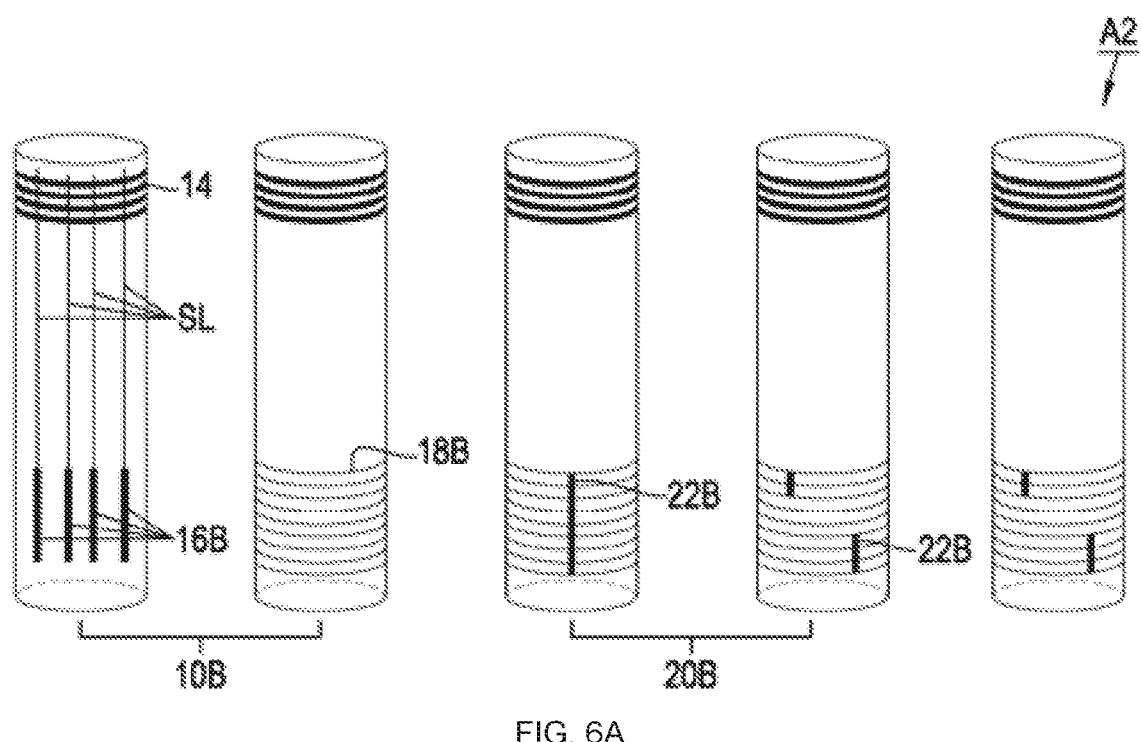
FIG. 6A shows a configuration of a lead structure A2 according to a third embodiment of the present invention.

FIG. 6A shows a configuration of a lead structure A2 according to a third embodiment of the present invention. The lead structure A2 of the third embodiment also includes a lead 10B and a lead case 20B, like the lead structure of the first embodiment.

In the lead 10B of the third embodiment, unlike the lead 10A of the first embodiment, a plurality of first electrodes 16B are arranged at uniform intervals within about 180° in a circumferential direction, not in a longitudinal direction, and the first electrodes 16B are connected to the second electrode 14 of an interface portion by the signal line SL.

On the other hand, a plurality of slots 18B having an arc angle of 180° in the circumferential direction are apart from each other in a longitudinal direction and are formed in parallel on the opposite side in the circumferential direction with respect to a position where the first electrodes 16B are provided.

In a lower portion of the lead case 20B corresponding to an insertion portion of the lead, a plurality of conductive plates 21B having a ring shape are arranged one after another in a longitudinal direction in parallel to each other, and a contact point 22B protruding radially inward from an inner surface of each conductive plate is provided.

Each conductive plate 21B is configured to be able to rotate in the circumferential direction by an external force.

Figure 6B:
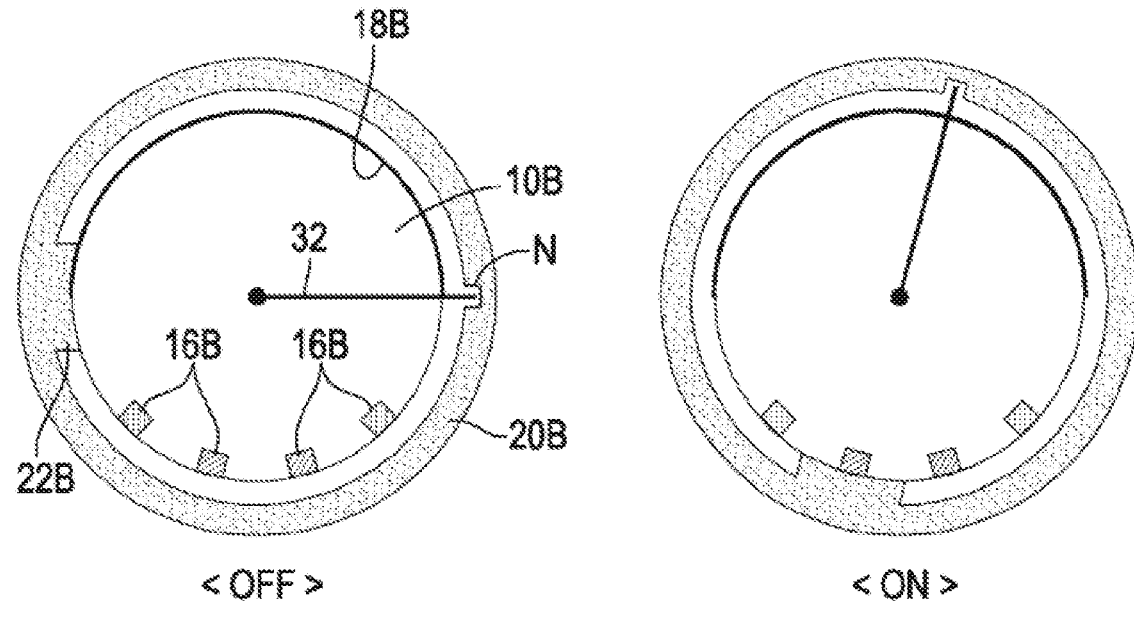
FIG. 6B shows a cross-sectional view of lead structure A2 of FIG. 6A.

As shown in FIG. 6B, a groove N is formed in the conductive plate 21B on the opposite side of the contact point 22B, and a tip of the plate key 32 may be inserted into the groove.

Accordingly, when the plate key 32 inserted into a hollow of lead 10B protrudes through a slot 18B into the case 20B and is inserted into the notch N, and rotates according to motor drive, and thus, a first electrode 16B of the lead 10B contacts the contact point 22B of the conductive plate 21B, the contact point 22B is in an ON state in which an electrical signal from the first electrode 16B is transmitted to the conductive plate 21B, otherwise the contact point 22B is in an OFF state, so that electrical connection is not made.

Because the plurality of first electrodes 16B are apart from each other in the circumferential direction of the lead 10B, by rotating the conductive plate 21B, the contact point 22B may selectively contact and electrically connect with the plurality of first electrodes 16B. In addition, some of the plurality of conductive plates 21B provided in the lead case 20B may be selectively energized with the first electrode 16B.

Figures 7A, 7B:
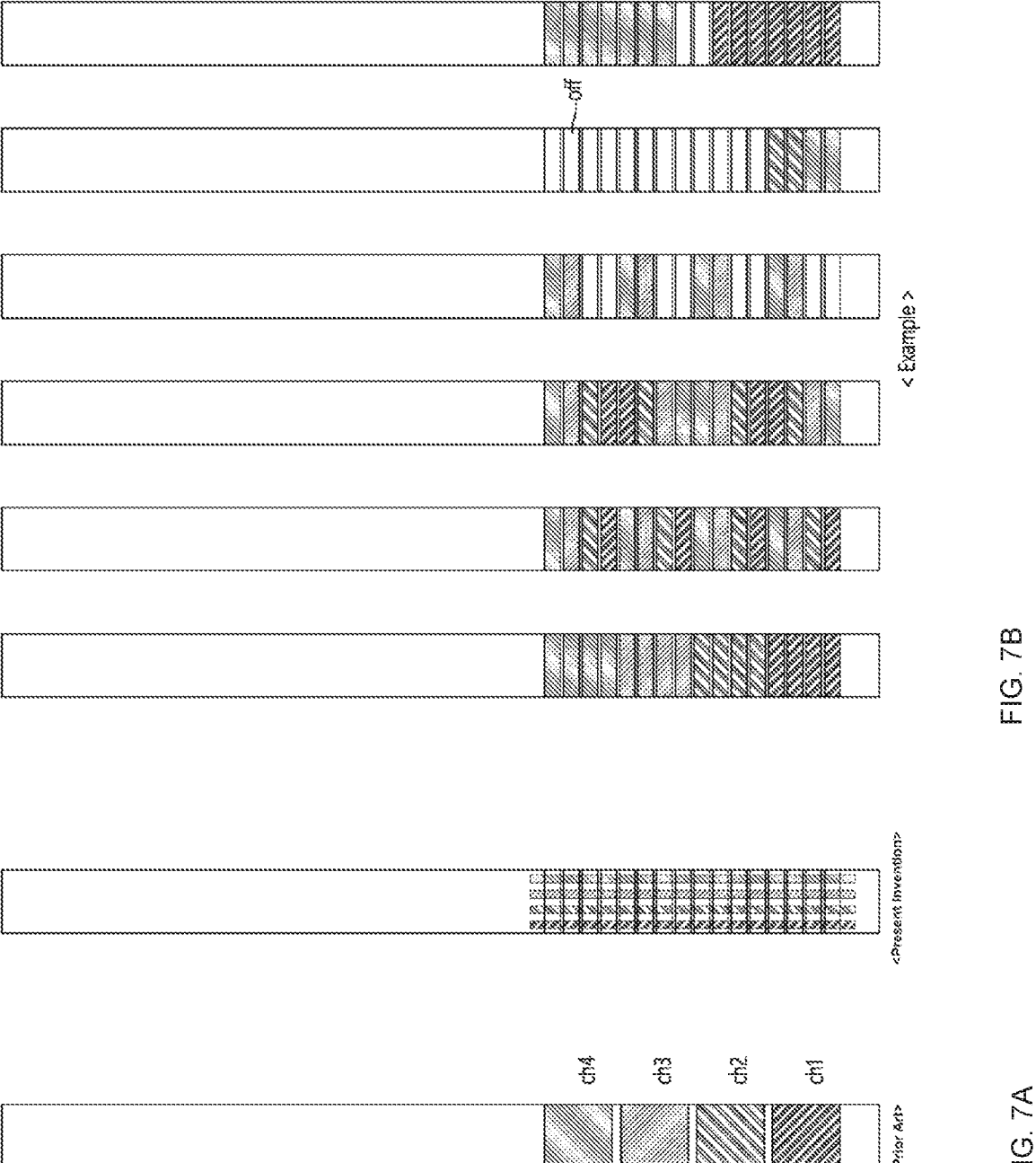
FIGS. 7A and 7B show a signal aspect obtained by the lead structure according to the third embodiment (FIG. 7B) with the prior art (FIG. 7A).

In this way, as shown in FIG. 7B, because a plurality of conductive plates are selectively connected to a specific electrode from among first electrodes or are not connected to the first electrodes, position and area to which electrical stimulation is applied may be finely adjusted in various combinations, as compared to the prior art shown in FIG. 7A.

Hereinafter, an operation of applying electrical stimulation to the deep brain using a lead structure configured as described above will be described.

An operator applies power to a lead system for a deep brain stimulator and performs an initialization process such as communication connection with an external device for zero adjustment and control of a conductive plate position.

Next, the operator inserts the lead structure A into a specific region of the brain according to a conventional lead insertion sequence. A hole is formed in a radial center of the electrode wire 10 of the lead structure at the time of insertion, and a guide wire is inserted therein to support the lead structure, but the guide wire is removed after insertion of the lead structure.

Next, after arranging the plate controller 30 in the hole where the guide wire was arranged, the plate controller is connected to a control unit (not shown) of the lead system for the deep brain stimulator.

On the other hand, the operator opens an electrode clamp, closes the electrode clamp according to a guide line, and connects an electrode contact of the electrode clamp to the second electrode 14 so that the electrode contact is in contact with the second electrode 14 in a correct position. This process is performed for a plurality of (e.g., four) leads. The operator transmits a neural signal obtained from an electrode portion of each electrode wire to the control unit in real time, and calculates which point of the electrode is closest to a target.

Next, a motor is driven according to a control signal from the control unit, the plate key 32 moves to move each of the plurality of conductive plates to a target position, and positions and intervals of target electrodes are adjusted using a signal generated accordingly.

At this time, when the conductive plate reaches a target point or receives a stop signal, the operator stops driving the motor and repeats this process to determine the final intervals and positions of electrodes. Next, the operator disconnects the conductive plate from the control unit, and removes the electrode clamp and the plate controller.

In the description of the above embodiment, the case of using a lead and a lead system according to the present invention for deep brain stimulation has been described. However, in addition to the above-described embodiment, the lead and lead system according to the present invention may be widely used to relieve pain or treat diseases by applying electrical stimulation to body organs, such as spinal cord stimulation for pain relief, frontal nerve stimulation for dysuria, and vagus nerve stimulation for epilepsy or depression.

The invention claimed is:

1. A lead structure configured to apply electrical stimulation to body organs, the lead structure comprising:
a lead comprising an electrode wire having one end provided as an insertion portion to be inserted into a body and the other end provided as an interface portion for connection with an external device, a first electrode in the insertion portion to transmit electrical stimulation to body organs, a second electrode on the interface portion to receive electrical stimulation applied from outside, and a signal line configured to interconnect the first electrode and the second electrode and transmit the electrical stimulation received by the second electrode to the first electrode; and
a lead case configured to surround the lead,
wherein a key hole penetrating from an inside to an outer surface is formed in a longitudinal direction at a position of the first electrode in the electrode wire,
a slot extending in the longitudinal direction is formed at the position of the first electrode in the lead case,
a conductive plate configured to apply electrical stimulation to body organs and a support plate configured to provide electrical stimulation from the first electrode to the conductive plate by contacting the first electrode are provided,
wherein the conductive plate and the support plate are provided on an outer surface and an inner surface of the lead case, respectively, and are coupled to each other with the slot therebetween to form a pair, and a plurality of pairs of a conductive plate and a support plate are provided and arranged to be movable along the slot.

2. The lead structure of claim 1, wherein the conductive plate and the support plate are coupled by an elastic connecting member passing through the slot and movably arranged in the lead case.

3. The lead structure of claim 2, wherein the support plate is formed with a through hole into which a tip of a plate key for moving the support plate is inserted.

4. A lead system implanted in a body to apply electrical stimulation to body organs, the lead system comprising:
a main processor connected to an external device for communication and control;
one or more lead structures according to claim 1;
an electrode clamp for electrical connection with the lead; and
a controller for controlling a position of transmitting electrical stimulation in the lead.

5. The lead system of claim 4, wherein the controller comprises a key capable of movement in a longitudinal direction of an electrode wire and rotational movement in a circumferential direction, and the key is inserted into a hollow of the electrode wire to move or rotate a conductive plate along the slot.

\* \* \* \* \*